United States Patent [19]
Roane

[11] Patent Number: 5,382,161
[45] Date of Patent: Jan. 17, 1995

[54] ENDODONTIC GUTTA PERCHA PLACEMENT

[76] Inventor: James B. Roane, 707 SW. 24th St., Norman, Okla. 73069

[21] Appl. No.: 155,527

[22] Filed: Nov. 22, 1993

Related U.S. Application Data

[63] Continuation of Ser. No. 785,043, Oct. 30, 1991, Pat. No. 5,286,193.

[51] Int. Cl.$^6$ .......................... A61G 5/02; A61C 5/02; A61C 5/04
[52] U.S. Cl. ...................... 433/81; 433/224; 433/90
[58] Field of Search ...................... 433/81, 89, 90, 224

[56] References Cited

U.S. PATENT DOCUMENTS

| | | | |
|---|---|---|---|
| 647,557 | 4/1900 | Cruttenden | 433/90 |
| 881,469 | 3/1908 | Hale | 433/81 |
| 1,189,735 | 7/1916 | Quintin | 433/81 X |
| 2,225,900 | 12/1940 | Bower | 32/60 |
| 2,486,056 | 10/1949 | Oclassen | 128/261 |
| 3,534,476 | 10/1970 | Winters | 433/224 |
| 3,863,345 | 2/1975 | Malmin | 32/15 |
| 3,968,567 | 7/1976 | Nevins | 32/15 |
| 4,357,136 | 11/1982 | Herskovitz et al. | 433/224 |
| 4,362,508 | 12/1982 | Söderström | 433/81 |
| 4,492,576 | 1/1985 | Dragan | 433/90 |
| 4,758,156 | 7/1988 | Johnson | 433/81 |
| 4,767,326 | 8/1988 | Bennett et al. | 433/90 |
| 4,798,596 | 1/1989 | Mühlbauer | 604/218 |
| 4,820,306 | 4/1989 | Gorman et al. | 433/81 X |
| 4,894,011 | 1/1990 | Johnson | 433/81 |
| 4,904,437 | 2/1990 | Mühlbauer | 264/295 |
| 4,911,641 | 3/1990 | Detsch | 433/228.1 |
| 4,952,209 | 8/1990 | Mühlbauer | 604/218 |
| 5,067,900 | 11/1991 | McSpadden | 433/81 |

FOREIGN PATENT DOCUMENTS

| | | |
|---|---|---|
| 0220551 | 5/1987 | European Pat. Off. |
| 1602331 | 12/1970 | France |
| 611164 | 5/1979 | Germany |
| 41801 | 5/1962 | Luxembourg |

OTHER PUBLICATIONS

Exhibit A–Cohen and Burns, *Pathways of the Pulp* (1976), pp. 351–355.
Exhibit B–Texceed Corporation advertisement entitled "Easy As . . . 1. 2. 3.". This document is undated but is admitted to be prior art.
Exhibit C–The Hygenic Corporation brochure entitled "Hygenic Ultrafil ™ Technique Manual". This document is undated but is admitted to be prior art.
Exhibit D–Thermafil brochure entitled "Thermafil Endodontic Obturators–Detailed Instructions for the use of Thermafil Endodontic Obturators", dated in 1991, and admitted to be prior art.
Exhbit E–Advertisement of Thermafil, dated in 1991, admitted to be prior art.
Exhibit F–Advertisement of AlphaSeal Endo System. This document is undated but is admitted to be prior art.
Exhibit G–Advertisement of Hygenic Corporation. This document is undated but is admitted to be prior art.
Exhibit H–Advertisement of JS Dental Manufacturing, Inc. (Undated but admitted to be prior art.).
Exhibit I–Advertisement of JS Dental Manufacturing, Inc. (Undated but admitted to be prior art.).
Exhibit J–Advertisment of JS Dental Manufacturing, Inc. (Undated but admitted to be prior art).

(List continued on next page.)

*Primary Examiner*—Nicholas D. Lucchesi
*Attorney, Agent, or Firm*—Dougherty, Hessin, Beavers & Gilbert

[57] ABSTRACT

A prefilled disposable apparatus is provided for placing thermoplastic filling material including gutta percha in an endodontically prepared root canal. A hollow carrier has a distal end and a proximal end and has a cylindrical carrier bore defined therethrough. A plug of thermoplastic filling material is contained in the carrier bore. A displacing shaft is received in the proximal end of the carrier bore for displacing the thermoplastic filling material from the distal end of the carrier bore into the endodontically prepared root canal.

43 Claims, 2 Drawing Sheets

OTHER PUBLICATIONS

Exhibit K–Advertisement of Johnson & Johnson (Undated but admitted to be prior art).
Exhibit L–Catalog description of device (Undated but admitted to be prior art).
Exhibit M–Illustration (Undated but admitted to be prior art).
Actual sample of prior art gutta percha point.
Exhibit A to Supplemental Information Disclosure Statement–Communication from European Patent Office re Application No. 92309372.8 dated May 7, 1993.
Exhibit B to Supplemental Information Disclosure Statement–English translation of French Patent 1,602,331.

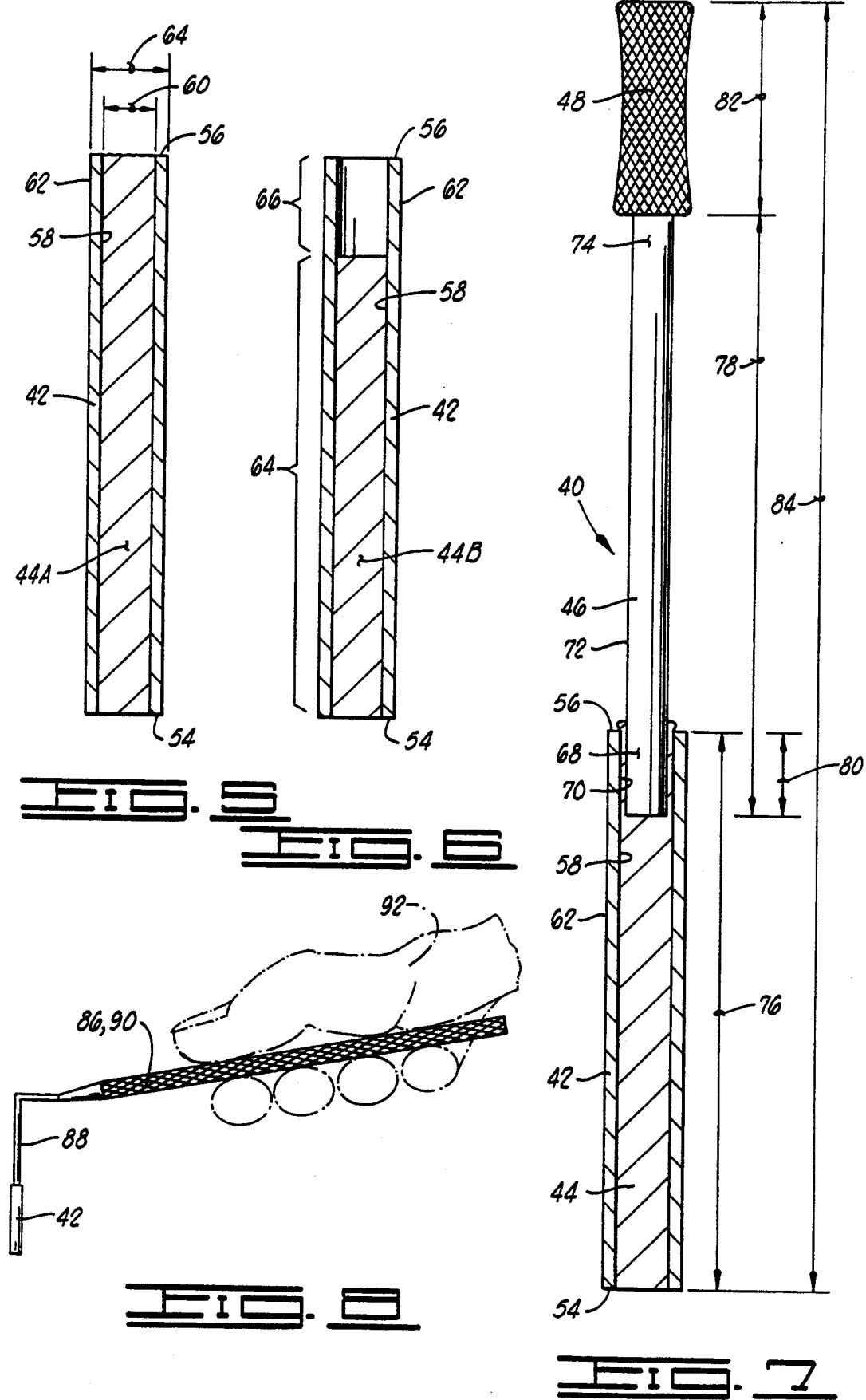

ENDODONTIC GUTTA PERCHA PLACEMENT

This is a continuation of copending application Ser. No. 07/785,043 filed on Oct. 30, 1991 now U.S. Pat. No. 5,286,193.

BACKGROUND OF THE INVENTION

1. Field of the Invention

The present invention relates generally to methods and apparatus for filling an endodontically prepared root canal, and more particularly, but not necessarily by way of limitation, to methods and apparatus for filling such a root canal with a thermoplastic material including gutta percha.

2. Description of the Prior Art

During endodontic procedures commonly referred to as root canal operations, one step of the procedure involves the filling of the root canal after it has been endodontically prepared, that is after it has been reamed out to remove pulpal tissue.

Endodontically prepared root canals are filled with a material commonly referred to as gutta percha. Gutta percha is commercially available in the form of gutta percha points which are elongated, tapered articles having a length of approximately twenty-eight mm and having a diameter of between approximately 0.15 to 1.4 mm. These gutta percha points may be held with tweezers or the like and inserted into the root canal. Once in place, they may be heated with a warmed instrument. A pick-shaped instrument commonly referred to as a condenser is then used to gradually push the softened gutta percha material down into the root canal to fill the root canal space.

There are many difficulties with this conventional use of gutta percha points. First, the points are difficult to handle, and a great deal of dexterity is required to place softened gutta percha points into the root canal opening and to compact that material so as to completely fill the root canal.

Several attempts have been made to improve upon methods and apparatus for placement of gutta percha material in an endodontically prepared root canal.

One approach is to use what is referred to as a gutta percha gun which is a device which heats a bulk quantity of gutta percha material and then forces the material through a hollow needle to place it in the root canal. One example of such a gutta percha gun is shown in U.S. Pat. No. 4,357,136 to Herskovitz et al.

Another approach has been to form the gutta percha material about an elongated shaft made of plastic or metal. The shaft with the material formed thereabout can be manually placed in the prepared root canal, and then the shaft is broken leaving a portion of the broken shaft along with the surrounding gutta percha material in place filling the root canal. Examples of such devices are shown in U.S. Pat. Nos. 4,758,156 and 4,894,011 both to Johnson.

Both of the devices described above have serious shortcomings.

The gutta percha guns like that of the Herskovitz et al. patent are very expensive and are bulky to use.

The devices like those of Johnson having a shaft imbedded in the gutta percha material are undesirable because they leave foreign material, namely the broken shaft, in the root canal. This foreign material can be very difficult to remove in the event that there is a failure of the root canal operation and it is desired to remove the filling materials.

Thus there is a need for a simple inexpensive means for placing gutta percha material in an endodontically prepared root canal. Further, there is a need for such means that provides a filling that does not include any foreign matter other than the gutta percha material.

SUMMARY OF THE INVENTION

The present invention provides a prefilled disposable apparatus for placing gutta percha filling material in an endodontically prepared root canal. The apparatus includes a hollow disposable carrier for storing the filling material prior to use and for carrying the filling material to a position adjacent an opening to the root canal for displacement into the root canal. The carrier is a segment of straight cylindrical tubing having first and second ends and having a constant diameter cylindrical outer surface extending from the first end to the second end, and having a constant diameter carrier bore defined through the tubing from the first end to the second end. The carrier bore contains a filling material which preferably is a thermoplastic filling material including gutta percha.

The carrier is used in conjunction with a displacing shaft which is received in the carrier bore for displacing the filling material from the carrier bore into the endodontically prepared root canal.

Numerous objects, features and advantages of the present invention will be readily apparent to those skilled in the art upon a reading of the following disclosure when taken in conjunction with the accompanying drawings.

BRIEF DESCRIPTION OF THE DRAWINGS

FIG. 1 shows a tooth which has been opened in the crown area to provide access to the interior of the tooth. Both of the root canals of the tooth have been endodontically prepared.

FIG. 2 shows the closing of the apical foramen of the root canal in the left side of the figure.

FIG. 3 shows the apparatus of the present invention placed adjacent the opening to the left-hand root canal in preparation for displacement of the filling material into the root canal to complete the filling thereof.

In FIG. 4, the displacing shaft has been pushed down through the carrier to displace the filling material into the root canal.

FIG. 5 is an elevation cross-section view of one form of prefilled disposable carrier in which the carrier bore is completely filled with filling material.

FIG. 6 is an elevation sectioned view of a second form of prefilled disposable carrier wherein only a first portion of the carrier bore has been filled with filling material leaving a second portion of the carrier bore open for receipt of a displacement shaft.

FIG. 7 is an elevation sectioned view of another embodiment of the invention wherein the prefilled disposable carrier is preassembled with a straight displacing shaft having a fingertip handle.

FIG. 8 is a side elevation view of another form of displacement shaft which is formed transversely on an elongated handle.

DETAILED DESCRIPTION OF THE PREFERRED EMBODIMENTS

Figure 1:
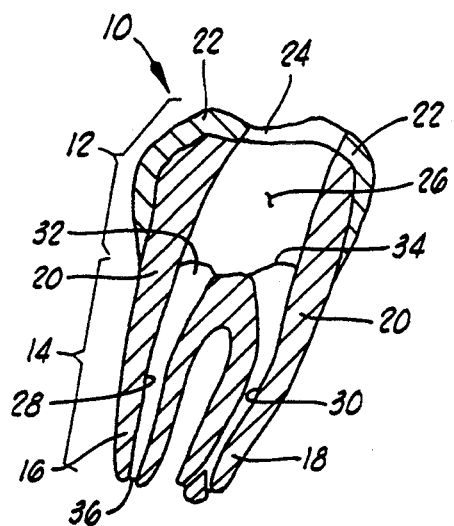
FIGS. 1–4 comprise a sequential series of illustrations showing the use of the apparatus of the present invention to fill an endodontically prepared root canal.

FIG. 1 shows a cross-sectional view of a tooth which has been endodontically prepared. The tooth is generally designated by the numeral 10. It has a crown portion 12 and a root portion 14 made up of first and second roots 16 and 18. The tooth is composed of dentine material 20 with the crown 12 being covered by enamel 22.

In FIG. 1, a portion of the enamel and dentine have been broken away from the crown 12 to form an access opening 24 providing access to the interior 26 of the crown. The pulpy material originally present within the crown interior 26 and root canals 28 and 30 has been removed by conventional endodontic procedures. The root canals 28 and 30 have been endodontically prepared by reaming in a well known manner.

The crown interior 26 and access opening 24 provide access to openings 32 and 34 to root canals 28 and 30, respectively.

Each root canal such as root canal 28 ends in an apical foramen 36 which is a small opening through which the nerve tissue originally entered the tooth.

Figure 2:
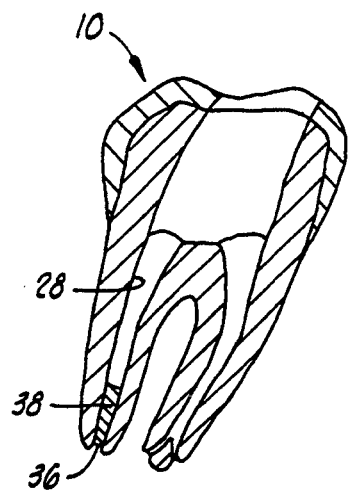

In FIG. 2, the apical foramen 36 of root canal 28 has been closed in a conventional manner by the placement of gutta percha material 38 therein. This is a conventional step which is performed by taking a conventional gutta percha point and dipping it in chloroform, then inserting the point into the canal so that the lower end of the point will conform to the shaft of the canal adjacent the apical foramen 36. The point is then removed and the chloroform is allowed to evaporate. The point is then coated with a sealing cement and reinserted. A heated instrument is then used to cut off the molded end portion of the gutta percha point thus leaving an initial gutta percha block or plug 38 as shown. This apical filling of gutta percha is subsequently molded into the canal area by compressing its upper surface with a condenser instrument.

It is after the initial blocking of the apical foramen as shown in FIG. 2, that the process of the present invention varies from prior art processes.

Figure 3:
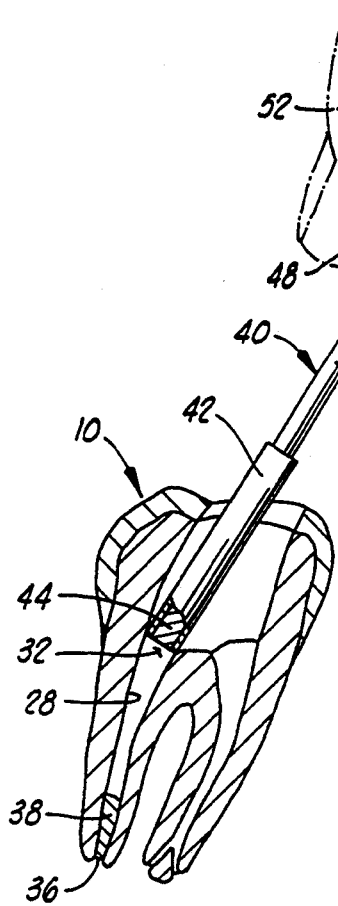

In FIG. 3, the prefilled gutta percha placement apparatus of the present invention is shown and generally designated by the numeral 40. The apparatus 40 has been inserted in the tooth 10 to a position adjacent the opening 32 to root canal 28. As is further described below, prior to placement of the device 40 as shown in FIG. 3, it is heated to soften the filling material contained therein.

The gutta percha placement apparatus 40 includes a carrier 42 containing a plug 44 of filling material. The apparatus 40 also includes a displacing shaft 46 having a fingertip handle 48 attached thereto.

In FIG. 3, the fingertip handle 48 is shown being grasped between the thumb 50 and forefinger 52 of a physician as shown in phantom lines.

Figure 4:
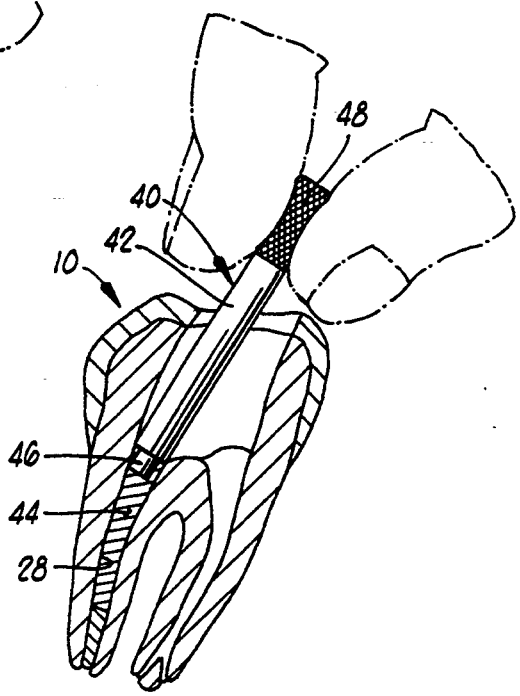

In FIG. 4, the displacing shaft 46 has been pushed downward through the carrier 42 to displace the filling material 44 into the root canal 28 thus filling the same.

FIG. 7 shows an elevation sectioned view of the apparatus 40 in a position analogous to that shown in FIG. 3 prior to displacement of the filling material 44 from the carrier 42.

The carrier 42 is constructed from a straight segment of hollow tubing. Carrier 42 has a distal end 54 and a proximal end 56. A cylindrical carrier bore 58 is defined through carrier 42 from the distal end 54 to the proximal end 56. Carrier bore 58 has a constant diameter 60.

The carrier 42 also has a straight cylindrical outer surface 62 extending from proximal end 56 to distal end 54. Cylindrical outer surface 62 has a constant diameter 64.

The carrier 42 can be generally described as a hollow disposable carrier means for storing the filling material 44 for an indefinite time prior to use and for carrying the filling material 44 to a position adjacent the opening 32 to the root canal 28 for displacement into the root canal 28 as illustrated in FIGS. 3 and 4.

The prefilled carrier 42 may be provided separate from the displacing shaft 46, so that the carrier 42 and displacing shaft 46 are assembled by the physician shortly prior to use, or the carrier 42 and displacing shaft 46 may come preassembled as shown in FIG. 7.

If the prefilled carrier 42 is provided to the physician separate from the displacing shaft 46, it can be provided in either of the two embodiments shown in FIGS. 5 and 6.

In the embodiment of FIG. 5, the plug of filling material indicated by 44A occupies the entire carrier bore 58. In the embodiment of FIG. 6, the plug of filling material designated as 44B occupies only a first portion 64 which may also be referred to as a distal portion 64 of carrier bore 58 adjacent the distal end 54 of carrier 42 thus leaving an unoccupied proximal portion 66 of carrier bore 58.

The second portion 66 of carrier bore 58 should have a length of at least about 2 mm to accommodate the overlapping engagement through distance 80 of approximately that same length as shown in FIG. 7. The shaft 46 may be inserted somewhat into the distal portion 64 so as to displace some of the filling material into the area 70 so as to hold the shaft 46 in place. In both FIGS. 5 and 6, the plug of filling material 44A or 44B can be said to occupy at least a distal portion of the carrier bore 58 adjacent the distal end 54. In FIG. 5, the filling material occupies the entirety of the carrier bore 58, while in FIG. 6, the filling material occupies less than the entire bore and the distal portion includes the portion 64 indicated in FIG. 6.

FIG. 7 illustrates the preferred manner of assembly of displacing shaft 46 with either form of prefilled carrier as shown in either FIGS. 5 or 6. To assemble the displacing shaft 46 with the prefilled carrier 42, an inner end portion 68 of displacing shaft 46 is first heated, preferably over an open flame such as a Bunsen burner, and is then inserted into the proximal end 56 of carrier bore 58 into engagement with the filler material 44 thus softening a small portion of the filler material 44 which will flow up through the slight annular clearance between displacing shaft 46 and carrier bore 58 thus forming a thin cylindrical portion 70 of filling material between the carrier bore 58 and the outer surface 72 of displacing shaft 46. The tackiness of the gutta percha material causes it to adhere to the inner end 68 of displacing shaft 46 so as to hold the displacing shaft 46 and prefilled carrier 42 together as they are being handled by the physician and placed in operative relationship to the tooth 10 as illustrated in FIGS. 3 and 4.

Alternatively the shaft 46 could be magnetized to aid in holding the carrier 42.

The displacing shaft 46 is sufficiently closely received within the carrier bore 58 to displace the plug of filling material 44 therefrom after the plug 44 has been heated without any separate sealing ring between the displacing shaft 46 and the carrier bore 58.

The fingertip handle 48 may be described as being attached to an outer end portion 74 of displacing shaft 46.

In a preferred embodiment of the apparatus shown in FIG. 7, the carrier 42 has a length 76 of 16 mm. The shaft 46 has a length 78 extending beyond handle 48 of 18 mm with an overlap 80 of approximately 2 mm. The handle 48 has a length 82 of approximately 6 mm. This provides an overall length 84 for the apparatus 40 when in the extended position of FIG. 7 of approximately 38 mm. When the apparatus 40 is collapsed to the position shown in FIG. 4 approximately 2 mm of shaft 46 will extend outward from the distal end 54 of carrier 42.

With the embodiment as illustrated in FIGS. 3, 4 and 7 wherein the shaft 46 has a length greater than the length of carrier 42, the shaft 46 can be described as having a maximum insertion depth 78 greater than the carrier length 76 so that after the shaft 46 displaces the filling material 44 into the root canal 28, the shaft 46 compacts or condenses the filling material 44 into the root canal 28.

Alternatively, the apparatus 40 can be constructed so that when in the fully inserted position, the shaft 46 will be flush with distal end 54 of carrier 42. In that design, 2 mm can be removed from shaft 46 so that the overall length 84 in the extended position will be no greater than about 36 mm.

With the overall length 84 being no greater than about 38 mm, the apparatus 40 may be entirely placed within a human patient's mouth if necessary to direct the plug 44 of filling material to be displaced from the carrier 42 directly into an endodontically prepared root canal 28 as shown in FIGS. 3 and 4.

More generally, the plug 44 of filling material occupying the distal portion of carrier bore 58 should have a length in the range of from about 10 mm to about 16 mm to provide sufficient material to fill one root canal. The carrier 42 should have a corresponding length approximately 2 mm longer than the necessary amount of filling material and thus should have a length in the range of from about 12 mm to about 18 mm. The carrier bore 58 should have a diameter 60 in the range of from about 1.0 mm to about 1.6 mm.

The carrier 42 is preferably constructed from commercially available stainless steel hypodermic tubing.

The displacing shaft 46 is preferably constructed from straight round stainless steel wire of an appropriate size to freely slide within the carrier bore 58 as illustrated. For example, regular wall 16 gauge hypodermic tubing has an inner diameter of 1.19 mm. With that tubing a displacing shaft having an outside diameter of 1.14 mm is used. A larger version may use 16X gauge tubing having an inner bore of 1.4 mm with which a displacing shaft having an outer diameter of 1.34 mm is used. A still larger version may use 14RW gauge tubing having an inner bore of 1.60 mm with which a displacing shaft having an outer diameter of 1.54 mm is used.

The handle 48 is preferably a molded plastic handle of the type currently being used on endodontic files. It can either be molded in place about the shaft 46 or attached by adhesives.

Thus, the stainless steel carrier 42 and shaft 46 provide an apparatus which can be readily heated over an open flame such as a Bunsen burner. The stainless steel carrier 62 is a good thermal conducting material which will rapidly conduct heat to the filling material 44 contained therein to soften the filling material prior to displacing the filling material into the endodontically prepared root canal 28.

It is noted that when working on the molars located in the back portions of a patient's mouth, it may be difficult or impossible to properly orient the straight shaft apparatus 40, and in those situations a posterior displacement apparatus 86 as shown in FIG. 8 will be utilized. The posterior displacing apparatus 86 includes a straight cylindrical transverse extension 88 having dimensions comparable to the shaft 46. The transverse extension 88 is a displacing means 88 which is received in the carrier 42 in an identical fashion to that illustrated in FIG. 7 for the straight displacing shaft 46.

The use of the apparatus 86 eliminates the length of the fingertip handle 48 thus providing for easier placement in the tighter confines of the back of the patient's mouth where the molars are located. As illustrated in phantom lines in FIG. 8, the posterior displacing apparatus has an elongated handle 90 which is constructed to be gripped with all fingers and the thumb of the human physician's hand 92 in a golf-club-like grip or in a pen-like grip. This also allows for easier application of the necessary displacing pressure in hard-to-reach areas.

Preferred Gutta Percha Filling Materials

The preferred thermoplastic filling material 44 for use with the present invention is commonly referred to in the dental profession as gutta percha. It is noted, however, that technically the term gutta percha refers to a particular type of naturally occurring polymer material, and the commercially available materials referred to as gutta percha are in fact mixtures of purified natural gutta percha with other filler materials. The following description of both the natural and commercially available gutta percha materials is taken from Cohen and Burns, *Pathways of the Pulp*, pages 351–355 (1976). According to Cohen and Burns, gutta percha is the purified coagulated exudate from mazer wood trees indigenous to the islands of the Malay Archipelago. They state that before the addition of waxes, fillers and opacifiers, gutta percha is a reddish-tinged, gray translucent material, rigid and solid at ordinary temperatures. It becomes pliable at 25° C. (77° F.) to 30° C. (86° F.); it is a soft mass at 60° C. (140° F.); and it melts, partially decomposing at 100° C. (212° F.).

Cohen and Burns state that gutta percha is a high molecular weight naturally occurring polymer structured from the isoprene mer. Gutta percha is trans-polyisoprene. Two crystalline forms of trans-polyisoprene exist, differing only in single bond configuration and molecular repeat distance. These are referred to as the "alpha" and "beta" forms which are described in detail in the Cohen and Burns reference which is incorporated herein by reference. Depending upon the processing of the gutta percha material, a given sample of material may contain an admixture of the "alpha" and "beta" crystalline forms and amorphous states.

Cohen and Burns state that gutta percha points used as root canal core filling materials have been reported to contain 17% gutta percha, 79% zinc oxide, and 4% zinc silicate, or 15% gutta percha, 75% zinc oxide, and 10% waxes, coloring agents, anti-oxidation agents, and opacifiers. They state that chemical analysis of five commercially available brands of endodontic points revealed a content of: gutta percha from 18.9% to 21.8%, zinc oxide from 59.1% to 75.3%, heavy metal sulfates from 1.5% to 17.3%, and waxes and resins in amounts of from 1.0% to 4.1%.

The preferred filling material 44 as used in the present invention can be generally described as a thermoplastic filling material including gutta percha. This includes materials such as those commercially available gutta percha point materials described above which include natural percha and various fillers and other additives in the general percentages described by Cohen and Burns.

I have observed that some commercially available gutta percha materials are softer than others at normal room temperature. One preferred material is that manufactured by Vereinigte Dentalwerke of Munich, Germany, which is distributed in the United States by Premier Dental Products of Norristown, Pa.

Methods Of Operation

Methods of performing endodontic procedures utilizing the gutta percha placement device of the present invention can be described generally as follows.

Initially as shown in FIG. 1, the tooth 10 is prepared by removing a portion of the crown to create the access opening 24 and by then removing the pulpy material in the space 26 and in the root canals 28 and 30. The root canals 28 and 30 are endodontically prepared, i.e., they are reamed out, to have an opening 32 of approximately 1.4 mm.

Then, the apical foramen 36 is plugged with a thermoplastic material including gutta percha as indicated at 38. This is performed in a conventional manner by taking a commercially available gutta percha point, dipping it in chloroform, and then inserting it into the root canal to conform the lower end of the gutta percha point to the exact shape of the canal in the area indicated at 38. Then the gutta percha point is removed and the chloroform is allowed to evaporate. The gutta percha point is then covered with a commercially available sealer material such as Kerr pulp canal sealer, Grossman's root canal cement, etc. This sealer material is an adhesive which helps bond the filling material to the walls of the root canal.

Upon reinsertion of the conventional gutta percha point, a red-hot instrument is inserted into the root canal to cut off the gutta percha point leaving the portion indicated at 38. The gutta percha is heated with the red-hot instrument tip, and is then compacted in the area 38 with an unheated condenser.

While the sealer material which coats the remainder of the root canal 28 continues to be tacky, the apparatus 40 of the present invention is very quickly brought into use. The apparatus 40 is heated over a flame to soften the filler material 44 contained therein. Then apparatus 40 is placed adjacent the opening 32 to root canal 28 and the heated filler material 44 is displaced into the root canal 28 while the sealer on the walls thereof is still very tacky and adhesive.

The filler material 44 which has just been displaced from the carrier 42 is then compacted or condensed within the root canal 28 either by use of the extended end of the displacing shaft 46 or through use of a conventional, commercially available condenser tool.

Subsequently the other root canal 30 will be treated in a similar manner, and then the space 26 will be filled and access opening 24 closed by conventional techniques.

It is important that the filling of the root canal 28 be accomplished very rapidly so that the thermoplastic material can completely fill the root canal and be compacted therein before the sealer material begins setting up and losing its ability to bond the thermoplastic material to the dentine material defining the root canal 28. The apparatus of the present invention greatly enhances this operation in that it makes it much easier and quicker to place the thermoplastic material in the root canal as compared to conventional prior art techniques where gutta percha points must be skillfully placed and packed into the root canal using procedures which require a great deal of manual dexterity.

It is envisioned that the carrier 42 will be made commercially available to physicians either preassembled with a straight displacement shaft 46 as illustrated in FIG. 7, or in the form of a plurality of separate carriers 42 in association with one or more separate straight displacing shafts 46 and/or one of the posterior shafts 86 as seen in FIG. 8.

In these procedures, at least the carrier 42 is inserted entirely within the patient's mouth as seen in FIGS. 3 and 4. When using the straight displacement shaft 46, the entire displacement shaft 46 and carrier 42 may be entirely placed within the patient's mouth when treating teeth toward the front of the mouth. When treating molars toward the back of the mouth, the posterior displacement apparatus 86 of FIG. 8 may be utilized in which case the carrier 42 will still be entirely placed within the patient's mouth although the entire handle 90 will not.

Thus it is seen that the methods and apparatus of the present invention readily achieve the ends and advantages mentioned as well as those inherent therein. While certain preferred embodiments of the invention have been illustrated and described for purposes of the present disclosure, numerous changes may be made by those skilled in the art which changes are encompassed within the scope and spirit of the present invention as defined by the appended claims.

What is claimed is:

1. A prefilled apparatus for placing thermoplastic filling material in an endodontically prepared root canal comprising:

a hollow carrier having a distal end and a proximal end and having a cylindrical carrier bore defined therethrough from said distal end to said proximal end, said carrier being free of any external lateral protrusions for grasping of the carrier; a plug of thermoplastic filling material occupying a distal portion of said carrier bore, said plug terminating adjacent said distal end of said carrier, said distal portion being less than all of said carrier bore thus defining a proximal portion of said carrier bore unoccupied by said plug; and a displacing shaft means, received in said proximal portion of said carrier bore and held in place in said carrier bore by adhesion to said plug, for displacing said plug of thermoplastic filling material from a distal end of said carrier bore directly into said endodontically prepared root canal.

2. The apparatus of claim 1, wherein:
said filling material includes gutta percha.

3. The apparatus of claim 1, wherein:
said carrier has a length in the range of from about 12 mm to about 18 mm.

4. The apparatus of claim 1, wherein:
said plug of filling material occupying said distal portion of said carrier bore has a length in the range of from about 10 mm to about 16 mm.

5. The apparatus of claim 4, wherein:

said carrier bore has a diameter at its distal end in the range of from about 1.0 mm to about 1.6 mm.

6. The apparatus of claim 1, wherein:
said carrier is constructed of a thermal conducting material which can be flame heated to soften said plug of thermoplastic filling material prior to displacing said filling material into said endodontically prepared root canal.

7. The apparatus of claim 1, wherein:
said cylindrical carrier bore has a constant diameter from said distal end to said proximal end of said carrier.

8. The apparatus of claim 1, wherein:
said displacing shaft means is sufficiently closely received within said carrier bore to displace said plug of thermoplastic filling material without any separate sealing ring between said displacing shaft means and said carrier bore.

9. The apparatus of claim 1, wherein:
said displacing shaft means is a straight shaft means having an inner end received in said proximal portion of said carrier bore and having an outer end extending out of said proximal end of said carrier.

10. The apparatus of claim 9, further comprising:
a fingertip handle attached to said outer end of said displacing shaft means, said fingertip handle being constructed so that it may be entirely held between a human physician's thumb and forefinger.

11. The apparatus of claim 10, wherein:
said apparatus has an overall length from said distal end of said carrier to an outer end of said fingertip handle no greater than about 38 mm so that said apparatus may be entirely placed within a human patient's mouth to allow said plug of thermoplastic filling material to be displaced from said carrier directly into said endodontically prepared root canal.

12. The apparatus of claim 10, wherein:
said carrier has a carrier length defined from its proximal end to its distal end; and
said displacing shaft means has a maximum insertion depth defined from said inner end of said shaft means to said finger tip handle, said maximum insertion depth being greater than said carrier length so that after said shaft means displaces said filling material into said root canal said shaft means compacts said filling material in said root canal.

13. The apparatus of claim 1, wherein:
said shaft means has a constant outside diameter.

14. The apparatus of claim 1, wherein:
said displacing shaft means is a transverse extension of an elongated handle constructed to be gripped with all fingers and the thumb of a human physician's hand.

15. The apparatus of claim 1, further comprising:
a cylindrical layer of said thermoplastic filling material between said displacing shaft means and said proximal portion of said carrier bore.

16. The apparatus of claim 1, wherein:
said carrier is a length of straight cylindrical tubing having a constant diameter cylindrical outer surface from its distal end to its proximal end.

17. The apparatus of claim 1, wherein:
said carrier provides a means for storing said thermoplastic filling material for an indefinite time prior to use.

18. A prefilled apparatus for placing a filling material into an endodontically prepared root canal, comprising:

a hollow cylindrical carrier having a proximal end and an open unobstructed distal end, said distal end having an outside diameter small enough that said distal end can be received inside an endodontically prepared space of a human tooth, and having a constant diameter cylindrical carrier bore defined therethrough from said proximal end to said distal end;

a plug of thermoplastic filling material occupying a distal portion of said carrier bore adjacent said distal end;

a straight displacing shaft having an inner end received in said carrier bore in said proximal end of said carrier and engaging said plug, and having an outer end extending in a proximal direction out of said carrier bore; and a fingertip handle attached to said outer end of said displacing shaft, said fingertip handle having a longitudinal axis substantially coaxial to a length of said displacing shaft.

19. The apparatus of claim 18, wherein:
said plug of filling material includes gutta percha.

20. The apparatus of claim 18, wherein:
said carrier has a carrier length defined from said proximal end to said distal end; and
said displacing shaft has a maximum insertion depth defined from said inner end of said shaft to said fingertip handle, said maximum insertion depth being greater than said carrier length so that after said shaft displaces said filling material into said root canal, said shaft compacts said filling material in said root canal.

21. The apparatus of claim 18, wherein:
said carrier has a length in the range of from about 12 mm to about 18 mm.

22. The apparatus of claim 18, wherein:
said plug of filling material occupying said distal portion of said carrier bore has a length in the range of from about 10 mm to about 16 mm.

23. The apparatus of claim 22, wherein:
said carrier bore has a diameter at said distal end in the range of from about 1.0 mm to about 1.6 mm.

24. The apparatus of claim 18, wherein:
said carrier is constructed of a thermal conducting material which can be flame heated to soften said plug of filling material prior to displacing said filling material into said endodontically prepared root canal.

25. The apparatus of claim 18, wherein:
said apparatus has an overall length from said distal end of said carrier to an outer end of said finger tip handle no greater than about 38 mm so that said apparatus may be entirely placed within a human patient's mouth to allow said plug of filling material to be displaced from said carrier directly into said endodontically prepared root canal.

26. The apparatus of claim 18, wherein:
said displacing shaft is sufficiently closely received within said carrier bore to displace said plug of filling material without any separate sealing ring between said shaft and said carrier bore.

27. The apparatus of claim 18, wherein:
said displacing shaft is held in place within said carrier bore by adhesion with said filling material.

28. The apparatus of claim 18, further comprising:
a cylindrical layer of said filling material between said displacing shaft and said carrier bore.

29. The apparatus of claim 18, wherein:

said carrier is a length of straight cylindrical tubing having a constant diameter cylindrical outer surface from said distal end to said proximal end.

30. The apparatus of claim 18, wherein:
said carrier provides a means for storing said thermoplastic filling material for an indefinite time prior to use.

31. A prefilled apparatus for placing thermoplastic filling material in an endodontically prepared root canal, comprising:
a hollow carrier having an open unobstructed first end and a second end and having a cylindrical constant diameter carrier bore defined therethrough from said first end to said second end, said first end having an outside diameter small enough that said first end can be received inside an endodontically prepared space of a human tooth; and
thermoplastic filling material occupying at least a first portion of said carrier bore adjacent said open unobstructed first end.

32. The apparatus of claim 31, wherein:
said thermoplastic filling material includes gutta percha.

33. The apparatus of claim 31, wherein:
said thermoplastic filling material entirely occupies said carrier bore.

34. The apparatus of claim 31, wherein:
said first portion of said carrier bore occupied by said thermoplastic filling material is adjacent said first end of said carrier and is less than an entirety of said carrier bore, thus defining a second portion of said carrier bore adjacent said second end of said carrier and unoccupied by said thermoplastic filling material.

35. The apparatus of claim 34, wherein:
said second portion of said carrier bore defines a means for receiving a displacing shaft in engagement with said thermoplastic filling material.

36. The apparatus of claim 35, wherein:
said second portion of said carrier bore has a length of at least about 2.0 mm.

37. The apparatus of claim 36 further comprising a displacing shaft received in said second portion of said carrier bore.

38. The apparatus of claim 31, wherein:
said carrier has a length in the range of from about 12 mm to about 18 mm.

39. The apparatus of claim 31, wherein:
said first portion of said carrier bore occupied by said thermoplastic filling material has a length in the range of from about 10 mm to about 16 mm.

40. The apparatus of claim 31, wherein:
said diameter of said carrier bore is in the range of from about 1.0 mm to about 1.6 mm.

41. The apparatus of claim 31, wherein:
said carrier is constructed of a thermal conducting material which can be flame-heated to soften said thermoplastic filling material prior to displacing said thermoplastic filling material into said endodontically prepared root canal.

42. The apparatus of claim 31, wherein:
said carrier provides a means for storing said thermoplastic filling material for an indefinite time prior to use.

43. The apparatus of claim 31, wherein:
said carrier is a length of straight cylindrical tubing having a constant diameter cylindrical outer surface from said first end to said second end.

* * * * *